United States Patent [19]

Patchett et al.

[11] Patent Number: 5,141,954
[45] Date of Patent: Aug. 25, 1992

[54] ANTIFUNGAL CARBAZATE

[75] Inventors: Arthur A. Patchett, Westfield; Frank VanMiddlesworth, Fanwood, both of N.J.

[73] Assignee: Merck & Co., Inc., Rahway, N.J.

[21] Appl. No.: 737,613

[22] Filed: Jul. 30, 1991

[51] Int. Cl.$^5$ ............... A61K 31/35; C07D 309/10
[52] U.S. Cl. ............................. 514/459; 514/460; 549/417; 549/418
[58] Field of Search ............... 514/459, 460; 549/417, 549/418

[56] References Cited

U.S. PATENT DOCUMENTS 4,952,604 8/1990 Hensens et al. .................. 549/417

OTHER PUBLICATIONS

J. Organic Chem, Wright et al., vol. 47 No. 3, pp. 523-526, 1982.

Primary Examiner—C. Warren Ivy
Assistant Examiner—Ba K. Trinh
Attorney, Agent, or Firm—Alice O. Robertson; Raymond M. Speer

[57] ABSTRACT

A new carbazate represented by the formula

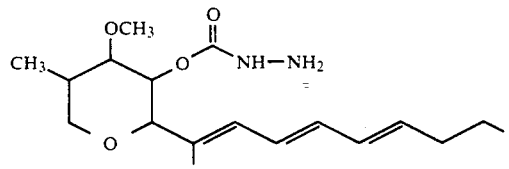

is found to be antifungal and especially useful in the treatment of mycotic infections caused by the Cryptococcus species.

3 Claims, No Drawings

ANTIFUNGAL CARBAZATE

The present invention is concerned with a novel carbazate having the formula

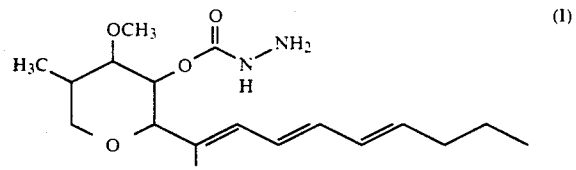

(1)

Compound I has the following spectral properties:

NMR SPECTRAL DATA $^1$H-NMR (300 MHz, CDCl$_3$) 0.89 (t, J=7 Hz, 3H), 1.10 (d, J=7 Hz, 3H), 1.42 (dt, J=7, 7 Hz, 2H), 1.81 (d, J=1 Hz, 3H), 2.09 (dt, J=7, 7 Hz, 2H), 1.81 (d, J=1 Hz), 3.36 (s, 3H), 3.28–3.65 (m, 3H), 3.56 (dd, J=2, 12 Hz, 1H), 3.78 (dd, J=2, 12 Hz, 1H), 4.94 (t, J=9 Hz, 1H), 5.68 (dt, J=7, 15 Hz, 1H), 5.95–6.35 (m, 6H).

MASS SPECTRAL DATA

MS (EI) m/z 338 (M)$^+$

The compound is a white solid, soluble in organic solvents. The compound has antifungal properties and is especially useful against the difficulty controllable Cryptococcus species. Moreover, the compound is stable against hydrolysis by serum rendering it useful as a treating agent.

The compound may be prepared by the following series of reactions from tetrahydro-4-methoxy-5-methyl-2-(1-methyl-1,3,5-nonatrienyl)-pyran-3-yl-glycine ((A); hereinafter Compound A):

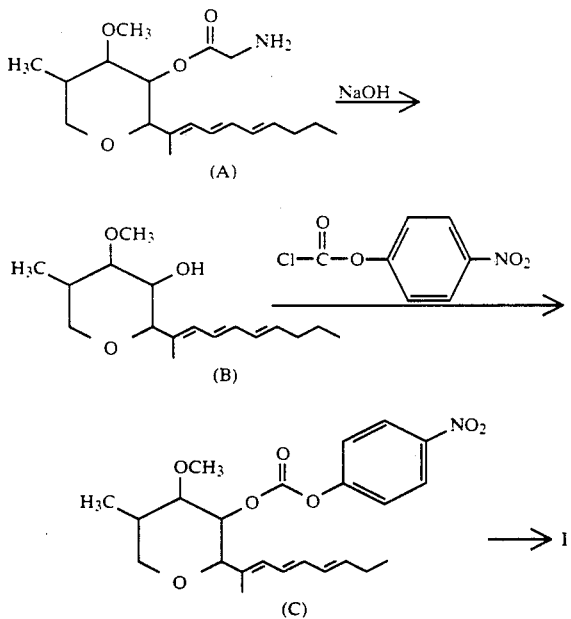

The starting material, Compound A, sometimes called restricticin, is a natural product obtained by the cultivation of Penicillium restrictum ATCC 20927 as described in U.S. Pat. No. 4,952,604.

In carrying out the preparation, Compound A is first hydrolyzed to obtain pyranol (Compound B) which is then esterified with an activated carbonate which when intimately contacted with hydrazine forms the carbazate.

The hydrolysis may be carried out in a conventional manner. Compound A is stirred together with a base. Although any conventional base may be employed, sodium hydroxide is convenient. The reaction is preferably carried out at ambient temperature for time necessary to complete the hydrolysis. Thereafter, Compound B may be recovered from the reaction mixture in a conventional manner.

A reactive ester such as a nitrophenyl carbonate is prepared in the next step. Other carbonates which may be employed include phosgene; and phenyl, p-bromophenyl, p-chlorophenyl and p-methoxyphenyl chlorocarbonate.

The preferred carbonate is p-nitrophenyl chlorocarbonate. In preparing the carbonate, an organic base such as quinoline is added to a solution of Compound B in an inert organic solvent such as methylene chloride. Other solvents such as carbon tetrachloride, ethylene chloride and the like, also may be employed. The solution of Compound B is then cooled in an ice bath under nitrogen atmosphere and p-nitrophenyl chlorocarbonate is added to the solution and the resulting mixture stirred for twelve to twenty hours. Completion of the reaction may be determined by the presence or absence of the starting material by TLC. After it has been determined that the reaction is complete, equal volumes of ethyl acetate and water are added to the mixture and intimately contacted and the product carbonate recovered in the ethyl acetate. The ethyl acetate solution is dried, the solvent removed from the dried solution to obtain the carbonate intermediate (Compound C). The ester may be purified by chromatography. Suitable adsorbents include "SEPHADEX" LH-20 (dextran adsorbent, Pharmacia).

The purified ester then is reacted with hydrazine. The reaction is preferably carried out in water miscible organic solvent such as tetrahydrofuran. The hydrazine is employed in aqueous solution and is generally added in a single portion whereupon a reaction starts to take place immediately. The reaction mixture is stirred for twelve to twenty hours to complete the reaction and to obtain Compound I. The latter is recovered using conventional procedures such as adding equal volumes of organic solvent and water, extracting the desired product into the organic solvent, thereafter recovering from the solvent and purifying by chromatography. Suitable organic solvents for the recovery are ethyl acetate, chloroform, ether, methylene chloride and the like. Ethyl acetate is preferred. The product may be obtained inpowder form by lyophilizing from benzene.

In each step, the presence of the intermediate and final product may be established by thin layer chromatography with ultraviolet absorption and charring when sprayed with 0.1M (NH$_4$)$_6$Mo$_4$O$_2$425 mM CeSO$_4$/3N H$_2$SO$_4$, or other oxidizing developer.

The compound of the present invention has antifungal activity toward certain yeast and other fungi. Moreover, the compound has activity in vivo, a property not possessed by a number of compounds which demonstrate in vitro activity.

The antifungal activity may be seen in a broth microdilution assay employing a yeast nitrogen base supplemented medium with 1 percent glucose (YNBD) supplement in which 0.15 ml of YNBD is dispensed into all wells of a 96 well microplate.

In carrying out the assay, Compound I was solubilized in 10% dimethyl sulfoxide (DMSO) and diluted to 2560 μg/ml. The compounds were then diluted to 256 μg/ml in YNBD and dispensed via a multichannel pipetter into the top row of a 96-well plate (each well containing 0.15 ml of YNBD), resulting in a drug concentration of 128 μg/ml. Compounds in the top row were diluted 2-fold down the columns yielding final drug concentrations ranging from 128–0.06 μg/ml. All tests were performed in duplicate.

A four-hour broth culture of *C. albicans* MY 1055 was adjusted using a spectrophotometer at 530 nm to equal a 0.5 McFarland standard. This yielded a cell concentration of $1-5 \times 10^6$ colony forming units (CFU)/ml. The 96-well microplates were inoculated using an MIC-2000 (Dynatech), which delivers 1.5 μl per well, yielding a final inoculum per well of $1.5-7.5 \times 10^3$ cells. One column per tray containing drug-free growth control wells was included.

After 24 hours of incubation, the microtiter plates were shaken gently on a shaker to resuspend the cells. The MIC-2000 inoculator was used to transfer a 1.5 microtiter sample from each well of the 96-well microtiter plate to a single reservoir inoculum plate containing Sabouraud dextrose agar (SDA). The inoculated SDA plates were incubated for 24 hours at 35° C. However, for *Cryptococcus neoformans* strains, SDA plates were inoculated at 48 hours and incubated 48 hours after being spotted on SDA before making minimum fungicidal concentration (MFC) readings.

The results were recorded as growth or no growth after 24 hours (48 hours for Cryptococcus strains) of incubation at 35° C. The MFC was defined as the lowest concentration of drug showing no growth or less than 4 colonies per spot on SDA. The results are summarized in the following table:

| Organism | MFC (μg/ml) |
|---|---|
| *Cryptococcus neoformans* | |
| MY 1051 | 4 |
| MY 1146 | 8 |
| MY 2061 | 8 |
| MY 2062 | 2 |
| *Candida albicans* MY 1055 | 2 |
| *C. pseudotropicalis* MY 2099 | 8 |
| *S. cerevisiae* MY 1976 | 8 |

The in vivo effectiveness of Compound I may be demonstrated in the mouse DBA/2 strain kidney assay.

Growth from an overnight SDA culture of *Candida albicans* MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum was $7.5 \times 10^4$ cells/mouse.

The assay then was carried out by administering 10 percent dimethyl sulfoxide suspensions of Compound I at various levels intraperitoneally (I.P.) twice a day (b.i.d.) for 4 days to 18–20 gram DBA/2 mice, which seven days previously had been infected with *Candida albicans* in the manner described above. Ten percent dimethyl sulfoxide was administered I.P. to *C. albicans* challenged mice as controls. After seven days, the mice were sacrificed by carbon dioxide gas, paired kidneys were removed aseptically and placed in sterile polyethylene bags containing 5 milliliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram kidney. The results of $10^{4.75}$ CFU/gm in the mice administered carbazate and $10^{6.5}$ CFU/gm in the mice administered DMSO indicate 98 percent removal of *C. albicans* from kidneys of mice when Compound I was administered I.P. to mice at 100 mg/kg, b.i.d. for 4 days.

The compounds may be utilized in various antifungal compositions. In such use, compounds may be admixed with a biologically inert carrier, generally with aid of a surface active dispersing agent, the nature of which would vary depending on whether the use is for the control of pathogens infecting man or animals.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of Compound I. The appropriate doses will vary depending on age, severity, body weight and other conditions. Generally, administration at 10–300 mg/kg body weight is believed to provide useful control of mycotic infections. For topical applications, the compositions are applied directly to the area where control is desired. For internal administration, the composition may be applied by injection or may be administered orally.

Therapeutic compositions may be presented in unit dosage form. The term "unit dosage form" refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

The following examples illustrate the invention but are not to be construed as limiting:

EXAMPLE I

A. Hydrolysis of Restricticin to Restrictinol (Compound B)

A solution of 500 microliters (500 mmol) of 1.0N sodium hydroxide was added with stirring to a solution of 50 milligrams (0.178 mmol) of restricticin (Compound A) in 5 milliliters of methanol at ambient temperature and stirring continued for two hours. At the end of this period, 80 milliliters of ethyl acetate and 40 milliliters of water were added to the mixture and the mixture thoroughly contacted. The layers were separated and the ethyl acetate layer washed with 40 milliliters of water. The washed ethyl acetate solution was dried over sodium sulfate and thereafter the solvents removed from the dried solution in vacuo to obtain 34 milligrams (78 percent yield) of the desired restrictinol (Compound B) as a slightly yellow oil. The oil exhibited a single spot by silica gel TLC (Rf 0.47, hexane: ethyl acetate (1:1)). It was detected by UV and by charring with 0.1M $(NH_4)_6Mo_7O_{24}/25$ mM $CeSO_4/3N$ $H_2SO_4$ of the TLC plate. (The charring was at 110° C. after spraying with the foregoing reagent). The NMR and MS spectra of the oily intermediate was as follows:

$^1$H-NMR (300 MHz, $CD_2Cl_2$) 0.90 (t, J=7 Hz, 3H), 1.01 (d, J=7 Hz, 3H), 1.42 (tq, J=7 Hz, 2H), 1.79 (d, J=7 Hz, 3H), 2.08 (ddt, J=1,7,7 Hz, 2H), 2.19 (m, 1H), 3.22 (dd, J=5, 9 Hz, 1H), 3.37 (s,3H), 3.43 (d, J=9 Hz, 1H), 3.56 (dd, J=9, 9 Hz, 1H), 3.58 (dd, J=3, 12 Hz, 1H), 3.77 (dd, J=2, 12 Hz, 1H), 5.74 (dt, J=7, 15 Hz, 1H), 6.09 (dd, J=1, 11 Hz, 1H), 6.12 (ddt, J=1, 10, 15 Hz, 1H), 6.22 (dd, J=10, 15 Hz, 1H), 6.36 (dd, J=11, 15 Hz, 1H).

$^{13}$C-NMR (75 MHz, $CD_2Cl_2$) 11.0, 12.4, 13.8, 22.8, 32.2, 35.3, 56.2, 68.1, 71.3, 84.7, 87.0, 126.3, 129.5, 131.0, 134.3, 134.6, 135.9.

MS (EI) M/Z 280 (m)$^+$

B. Formation of Carbonate Ester of Restrictinol (Compound C)

220 milligrams (0.79 mmol) of Compound B, prepared in the manner above described, was dissolved in 15 milliliters of methylene chloride and to the resulting solution was added 0.22 milliliter (1.8 mmol) of quinoline while the reaction mixture was cooled in an ice bath. 370 milligrams (1.8 mmol) of p-nitrophenyl chlorocarbonate then was added, and the reaction mixture stirred overnight under nitrogen atmosphere. After stirring 18 hours, the reaction mixture on testing for starting material by TLC was found to be complete. 30 milliliters of water and 30 milliliters of ethyl acetate were then added and shaken together. The layers were then separated and the organic layer first washed with 20 milliliters of 1.0 HCl, followed by 20 milliliters of saturated brine. The ethyl acetate solution was dried over sodium sulfate and thereafter, the solvent removed in vacuo from the dried solution to obtain 317 milligrams of dark crude oil.

The residue oil was dissolved in methanol and applied to a "SEPHADEX" LH-20 column (300 milliliters) equilibrated in methanol. The column was eluted at 2 ml/min and 12 milliliter fractions were collected. Fractions 21-26 (shown to be of same compound by TLC) were combined and the solvents removed to obtain the desired p-nitrophenyl chlorocarbonate of restrictinol (Compound C) as a creamy white semisolid in an amount of 314 milligrams (90 percent yield). The semisolid exhibited a single spot on silica gel TLC (Rf 0:52 hexane-diethyl ester (1:1)) by UV at 254 nm and charring with 0.1M $(NH_4)_6Mo_7O_{24}/23$ mM $CeSO_4/3N$ $H_2SO_4$. The NMR spectrum was as follows:

$^1$H-NMR (300 MHz, $CDCl_3$) 0.92 (t, 7 Hz, 3H), 1.12 (d, J=7 Hz, 3H), 1.45 (tq, J=7, 7 Hz, 2H), 1.80 (d, J=1 Hz, 3H), 2.12 (ddt, J=7, 7, 1 Hz, 2H), 2.28-2.38 (m, 1H), 3.41 (s, 3H), 3.67 (d, J=9 Hz, 1H), 3.51 (dd, J=5, 9 Hz, 1H), 3.61 (dd, J=3, 12 Hz, 1H), 3.88 (dd, J=2, 12 Hz, 1H), 4.81 (t, J=9 Hz, 1H), 5.74 (dt, J=7, 15 Hz, 1H), 6.05-6.42 (m, 4H), 7.24 (d, J=8 Hz), 7.51 (d, J=8 Hz), 8.20 (d, J=8 Hz), 8.37 (d, J=2 Hz).

C. Formation of Carbazate (Compound I)

113 milligrams (0.25 mmol) of Compound C, prepared in the manner described above in Part B, was dissolved in 5 milliliters of tetrahydrofuran and to the resulting solution was added 2.5 milliliters of a 35 percent aqueous hydrazine solution (containing 27 millimoles) in one portion. Immediately upon addition, a bright yellow color appeared. The mixture was stirred overnight; then, water and ethyl acetate were added and the mixture shaken together, the layers separated, and the organic solvents removed in vacuo to obtain a crude orange oil. The latter was dissolved in methanol and applied directly to a "SEPHADEX" LH-20 column (75 ml) which has been equilibrated in methanol. Three milliliter fractions were collected and fractions 21-23 (shown to be the same compound by TLC) were combined and subjected to reduced pressure to remove the methanol and yield 60 milligrams (71 percent yield) of the carbazate (Compound I) as a cream colored solid. The solid was lyophilized from benzene to a free flowing solid. The carbazate (Compound I) exhibited an Rf value of 0.25 on silica gel TLC in hexane-ethyl acetate (1:1). The compound was detected further on a TLC plate by UV at 254 nm, and also by charring with 0.1M $(NH_4)_6Mo_7O_{24}/25$ mM $CeSO_4/3N$ $H_2SO_4$. The compound exhibited the NMR and MS spectra previously given

EXAMPLE II 1000 compressed tablets each containing 500 mg of Compound I are prepared from the following formulation:

| Compound | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE III 1000 hard gelatin capsules, each containing 500 mg of Compound I are prepared from the following formulation:

| Compound | Grams |
| --- | --- |
| Compound I | 500 |
| Starch | 750 |
| Dibasic calcium phosphate hydrous | 5000 |

| Compound | Grams |
|---|---|
| Calcium stearate | 2.5 |

EXAMPLE IV 250 ml of an injectable solution are prepared by conventional procedures having the following formulation:

| | |
|---|---|
| Dextrose | 12.5 g |
| Water | 250 ml |
| Compound I | 400 mg |

The ingredients are blended and thereafter sterilized for use.

EXAMPLE V

An ointment suitable for topical application may be prepared by intimately dispersing 13 milligrams of Compound I in 1 gram of commercially available polyethylene/hydrocarbon gel.

What is claimed is:

1. A carbazate compound having the formula:

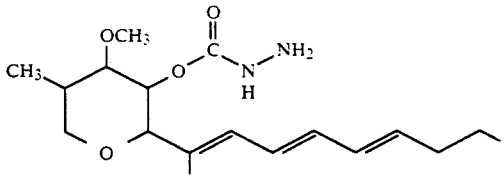

2. A composition comprising a therapeutic antifungal amount of the compound of claim 1 in admixture with a pharmaceutically acceptable carrier.

3. A method for controlling mycotic infections comprising administering to a subject in need of treatment an antifungal amount of the compound of claim 1.

* * * * *